US012779578B2

(12) United States Patent
Xia et al.

(10) Patent No.: US 12,779,578 B2
(45) Date of Patent: Nov. 3, 2026

(54) INTRINSIC PROCESS SIGNAL-BASED ONLINE SPATTER DETECTION METHOD FOR RESISTANCE SPOT WELDING, AND SYSTEM

(71) Applicant: SHANGHAI JIAO TONG UNIVERSITY, Shanghai (CN)

(72) Inventors: Yujun Xia, Shanghai (CN); Yan Shen, Shanghai (CN); Yongbing Li, Shanghai (CN); Haiyang Lei, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 1092 days.

(21) Appl. No.: 17/758,751

(22) PCT Filed: Jan. 7, 2021

(86) PCT No.: PCT/CN2021/070543
§ 371 (c)(1),
(2) Date: Jul. 13, 2022

(87) PCT Pub. No.: WO2021/147681
PCT Pub. Date: Jul. 29, 2021

(65) Prior Publication Data

US 2023/0083207 A1 Mar. 16, 2023

(30) Foreign Application Priority Data

Jan. 20, 2020 (CN) ......................... 202010064515.3

(51) Int. Cl.
*B23K 11/25* (2006.01)
*G01N 33/207* (2019.01)

(52) U.S. Cl.
CPC ............ *B23K 11/25* (2013.01); *G01N 33/207* (2019.01)

(58) Field of Classification Search
CPC ..... B23K 11/115; B23K 11/25; B23K 11/253; B23K 11/257; B23K 31/125;
(Continued)

(56) References Cited

U.S. PATENT DOCUMENTS 4,365,134 A * 12/1982 Eagar ..................... B23K 11/34 219/92
4,694,135 A * 9/1987 Nagel .................. B23K 11/256 219/110

(Continued)

*Primary Examiner* — Phuong T Nguyen
(74) *Attorney, Agent, or Firm* — CBM PATENT CONSULTING, LLC

(57) ABSTRACT

An intrinsic process signal-based online expulsion detection method for resistance spot welding process, which comprises: acquiring the intrinsic process signal and current signal output by sensors installed at two electrodes in real-time during the welding process and establishing a relationship graph; performing expulsion judgement based on the relationship graph to obtain expulsion frequency, single intrinsic process signal feature and an accumulated feature; calculating expulsion metal volume according to the accumulated feature and electrode profile features to obtain a prediction expulsion metal amount. The method performs online prediction of the expulsion metal amount according to the intrinsic process signal for resistance spot welding process, thereby achieving online quantitative estimation of the expulsion intensity, overcoming the defect of the traditional technology which relies on manual detection, and improving detection efficiency and accuracy.

6 Claims, 6 Drawing Sheets

(58) Field of Classification Search
CPC ..... B23K 11/185; B23K 11/16; B23K 11/002; B23K 26/244; B23K 9/028; B23K 9/173; B23K 9/007; B23K 9/0035; B23K 9/025; B23K 2101/18; B23K 2101/006; B23K 35/226; B23K 11/3009; B23K 11/256; G01N 33/207
USPC ........... 219/86.1, 91.2, 91.21, 109, 118, 119, 219/120, 127, 117.1
See application file for complete search history.

(56) References Cited

U.S. PATENT DOCUMENTS

| | | | | |
|---|---|---|---|---|
| 10,391,582 | B2 * | 8/2019 | Moision | B23K 11/115 |
| 2018/0111217 | A1 * | 4/2018 | Chai | B23K 11/20 |
| 2019/0344376 | A1 * | 11/2019 | Sawanishi | B23K 11/115 |

* cited by examiner

INTRINSIC PROCESS SIGNAL-BASED ONLINE SPATTER DETECTION METHOD FOR RESISTANCE SPOT WELDING, AND SYSTEM

TECHNICAL FIELD

The invention relates to the field of welding, in particular to an online detection method and system for resistance spot welding expulsion based on an intrinsic process signal.

BACKGROUND OF THE INVENTION

The resistance spot welding (RSW) process completes more than 80% of the assembly work for steel auto-body. Expulsion affects the body surface quality and positioning accuracy, and even affects the mechanical properties of the weld. In the prior art, the mass difference before and after expulsion is measured by means of manual stripping to obtain the quantity of the expulsion metal. However, this approach has a large workload, low measurement accuracy, and cannot achieve real-time online inspection.

SUMMARY OF THE INVENTION

In response to the defects in the prior art, the present invention provides a method and system for online detection of resistance spot weld expulsion based on intrinsic process signals. The method is low cost, time-efficient, highly accurate, applicable to multiple expulsion detection, and can be applied to welding production lines.

The present invention is achieved by the following technical scheme:

The invention relates to a method for online detection of resistance spot weld expulsion based on intrinsic process signals. First, the intrinsic process signals and current signals output from the sensors installed at the two electrodes are collected in real time during the welding process, and a relationship diagram of these signals over time is established. Then, the expulsion judgment is carried out based on this relation diagram to obtain the expulsion frequency and the signal feature of each expulsion. and they are subsequently combined to obtain the accumulated feature of the expulsion. Finally, the expulsion metal volume can be calculated from the cumulative feature and the electrode morphology feature, and thus the predicted value of the expulsion metal amount can be obtained.

The intrinsic process signals include dynamic resistance signal, dynamic electrode force signal, dynamic electrode displacement signal, acoustic emission signal and ultrasonic signal, wherein the dynamic resistance signal refers to a time-varying resistance between two electrodes during the RSW process; the dynamic electrode force signal refers to the time-varying force applied between the two electrodes during the RSW process; the dynamic electrode displacement signal refers to the relative distance change between the two electrodes during the RSW process; the acoustic emission signal refers to the stress wave propagating through the two electrodes during the RSW process; the ultrasonic signal refers to the ultrasonic wave propagating through the air during the RSW process.

The electrode cap comprises the shape of: a cylinder, a dome, a curved-top cone, a ball head, a truncated cone, or their combination, wherein the profile features of the electrode cap include: the electrode bottom diameter, the tip surface diameter, the tip surface curvature radius, and the cone angle.

The expulsion judgment refers to: in the heating stage, the expulsion is determined to begin when the derivative of intrinsic process signal with respect to time is equal to a preset threshold; after the expulsion starts, the expulsion is determined to end when the derivative of intrinsic process signal with respect to time is again equal to the preset threshold. The absolute amplitude difference between the intrinsic process signal corresponding to the expulsion beginning and ending moment is taken as a single feature.

Preferably, when multiple expulsions occur in a welding process, several single features of the intrinsic process signal are combined to obtain an accumulated feature.

The present invention relates to a system for implementing the above method, which includes calculation and analysis modules and the current signal acquisition module attached to them respectively, and an intrinsic process signal acquisition module, wherein the current signal acquisition module collecting the current signal is connected with the current sensors installed at the electrodes; the intrinsic process signal acquisition module collecting the intrinsic process signals is respectively connected with the intrinsic process signal sensors installed at the two electrodes; the calculation and analysis modules calculate the predicted amount of the expulsion metal according to the intrinsic process signal and the current signal.

Technical Effect

The invention solves the problems of large workload, low measurement precision and poor timeliness caused by manual means such as visual and indentation measurement in the existing welding production process, and solves the problem of difficulty in optimization of process parameters due to the inability to achieve real-time detection of expulsion.

Compared with the prior art, the invention realizes the real-time detection of the expulsion metal amount according to the intrinsic process signal and the current signal during the RSW process, and the online quantitative evaluation of the weld expulsion intensity. The shortcoming of traditional technology that relies on manual detection is overcome, and the detection efficiency is remarkably improved. Meanwhile, the invention considers the influence of shape of different electrode caps and exhibits a good linear correlation between the predicted and actually measured expulsion metal amount, indicating that the invention is highly applicable and has high detection precision. In addition, the invented on-line expulsion detection method has high calculation speed and low requirements for hardware systems, and is suitable for various RSW application scenarios.

Figure 1:
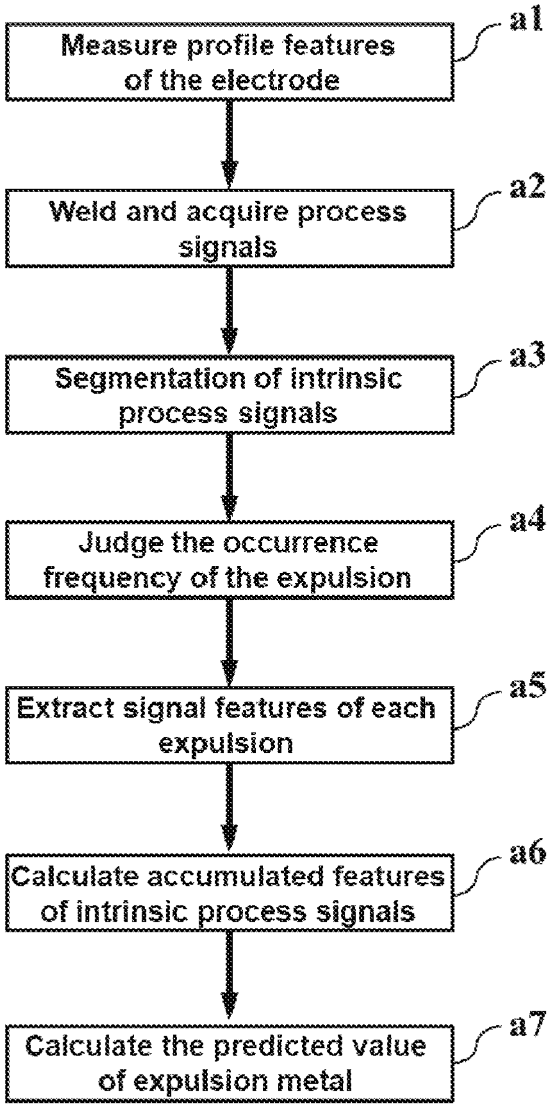
FIG. 1 is a flowchart of the method of the present invention.
Figure 3:
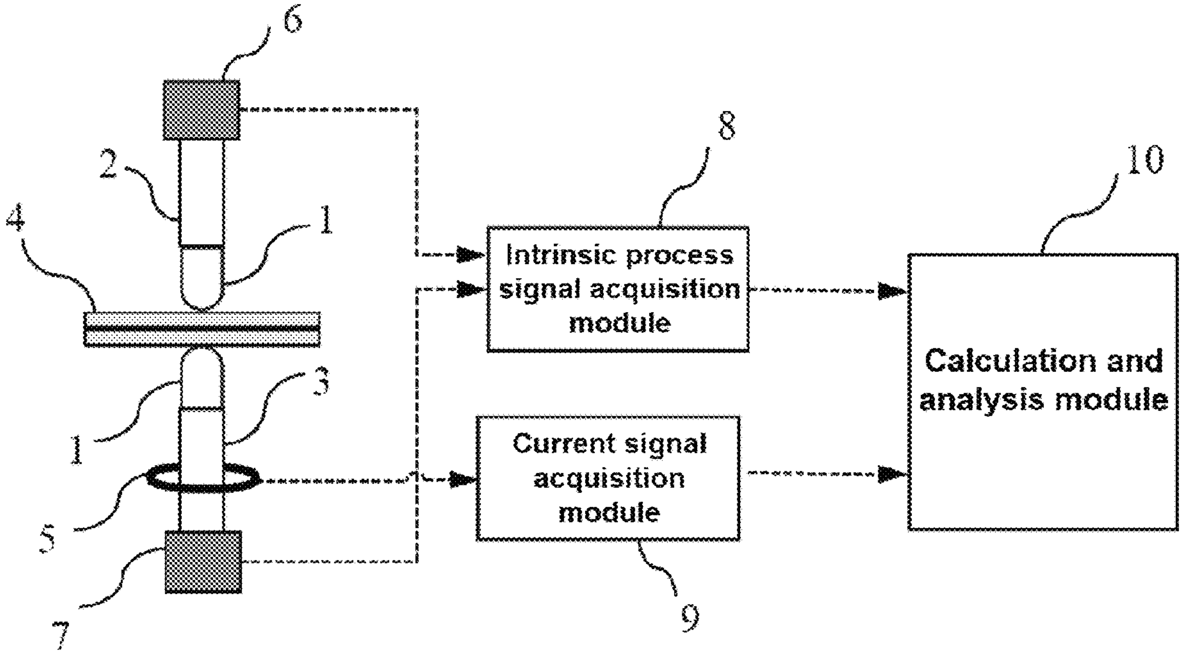
Figure 4:
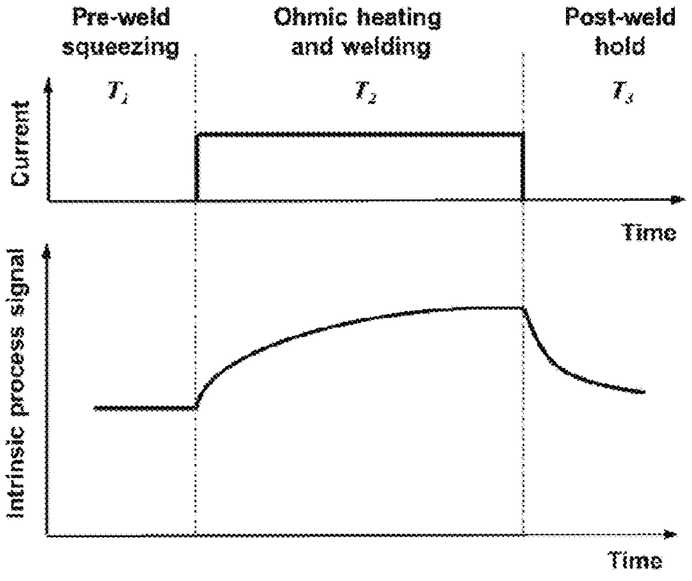
Figure 5:
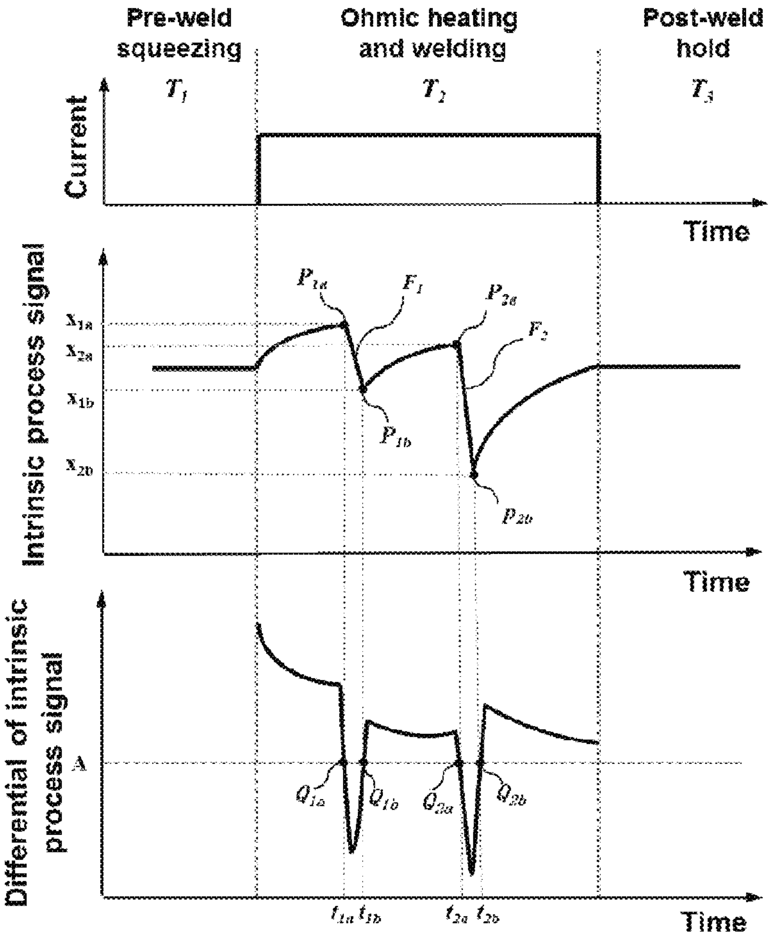
Figure 6:
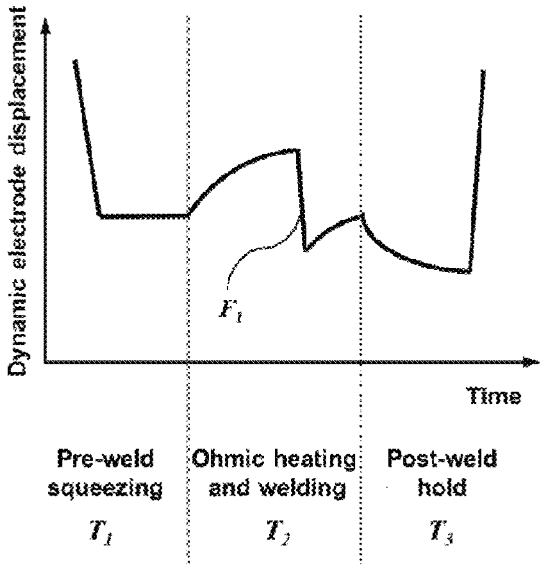
Figure 7:
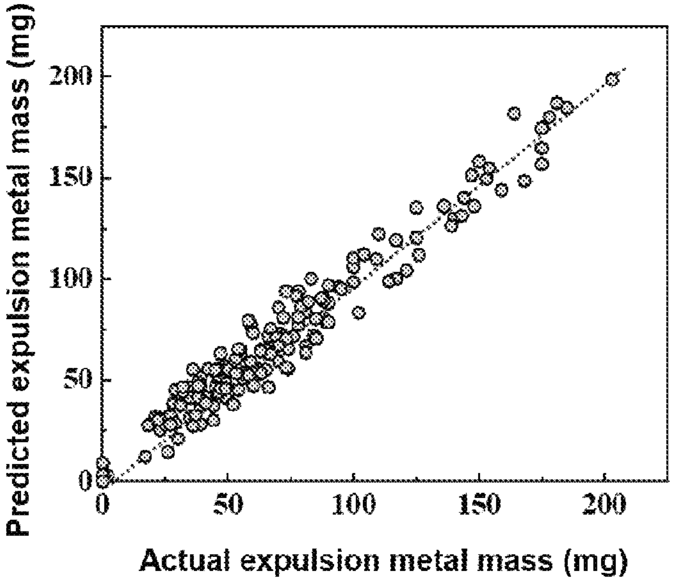
Figure 8:
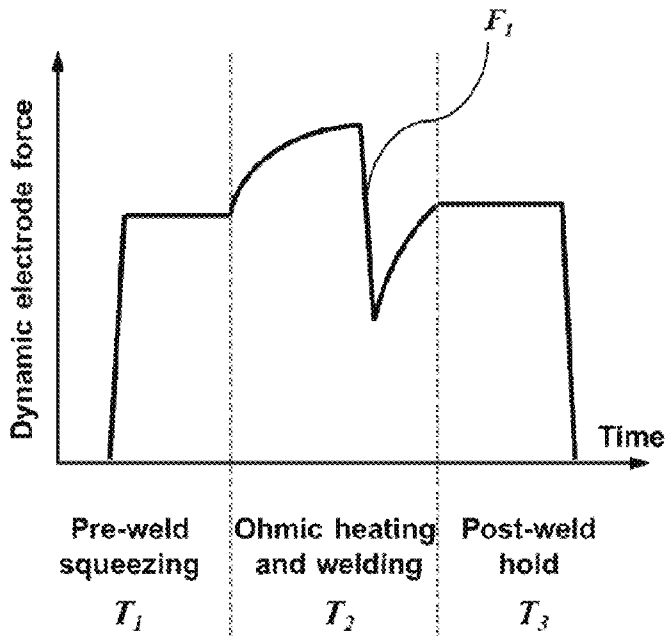
Figure 9:
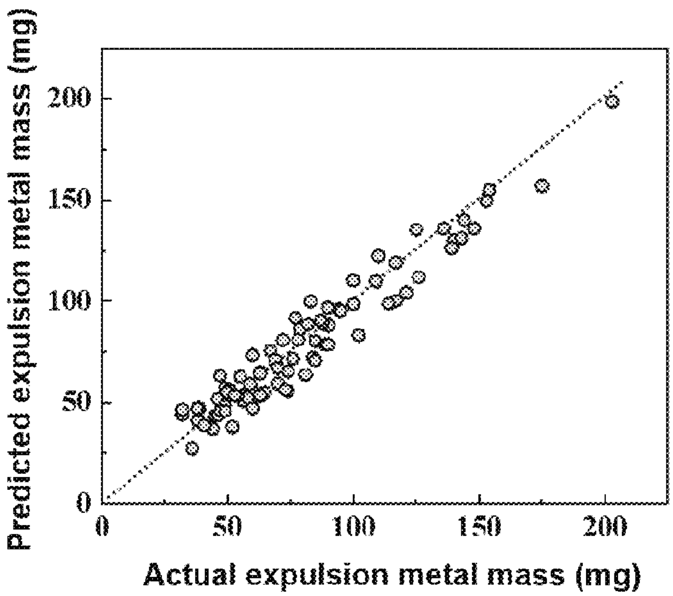

In the drawings: a is a domed electrode with a spherical tip face; b is a cone electrode with a spherical tip face; c is a ball-head electrode; d is a cylindrical electrode; e is a truncated cone electrode; f is a cylindrical electrode with a spherical tip face; D is the electrode bottom diameter; $D_t$ is the tip face diameter; $R_t$ is the tip surface curvature radius; 1 is the cone angle;

FIG. 3 is a schematic diagram of the system of the present invention;

In the figure, the electrode cap 1, the upper electrode 2, the lower electrode 3, the workpiece to be welded 4, the current sensor 5, the intrinsic process signal sensor installed at the upper electrode 6, the intrinsic process signal sensor installed at the lower electrode 7, the intrinsic process signal acquisition module 8, the current signal acquisition module 9, the calculation and analysis module 10;

FIG. 4 is a schematic diagram of segmentation of the intrinsic process signal during the RSW process;

FIG. 5 is a schematic diagram of expulsion identification and expulsion feature extraction;

FIG. 6 is a time evolution diagram of the dynamic electrode displacement signal for Example 1;

FIG. 7 is a scatter plot of predicted expulsion metal mass versus measured expulsion metal mass for Example 1;

FIG. 8 is a time evolution diagram of the dynamic electrode displacement signal for Example 2;

FIG. 9 is a scatter plot of predicted expulsion metal mass versus measured expulsion metal mass for Example 2;

In the figures, dashed lines are trend lines obtained by linear regression.

DETAILED DESCRIPTION OF THE PREFERRED EMBODIMENTS

Example 1

As shown in FIG. 1, the present example relates to an online detection method for RSW expulsion based on intrinsic process signals. First, measure the profile features of the electrode cap 1, perform welding and collect the welding current and the intrinsic process signals, and develop the relationship graph between the intrinsic process signal and time during the heating period. Then, judge the expulsion frequency based on this relationship and the expulsion criterion, extract each expulsion's single feature and make a combination to obtain the accumulated feature of the intrinsic process signal. This accumulated feature is used together with the profile features of electrode cap 1 to calculate the expulsion metal volume, and finally obtain the predicted expulsion metal amount.

Figure 2:
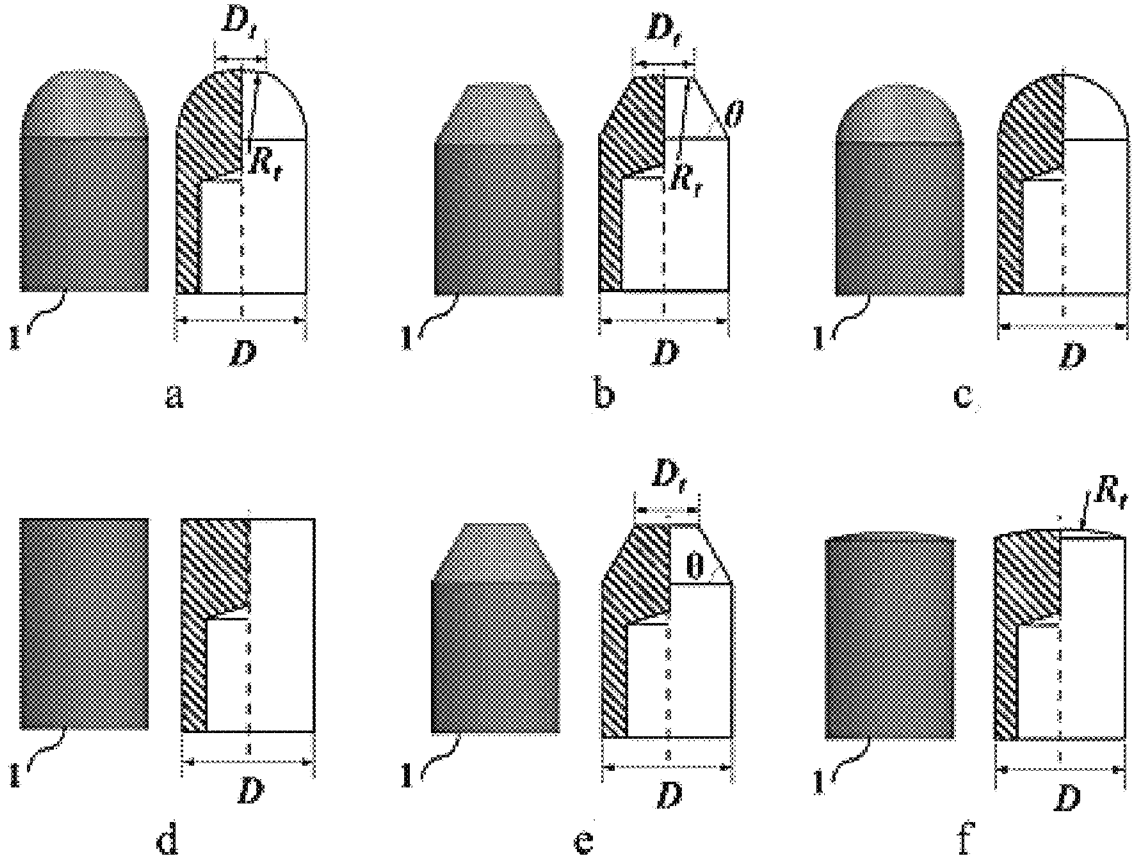
FIG. 2 is a schematic view of an electrode cap.

As shown in FIG. 2A, the electrode cap 1 of the present example is a domed electrode with a spherical tip face;

The profile features include the electrode bottom diameter, the tip face diameter, the tip surface curvature radius, and the cone angle.

The intrinsic process signals include the dynamic resistance signal, the dynamic electrode force signal, the thermal expansion electrode displacement signal, the acoustic emission signal, and the ultrasonic signal. The present embodiment preferably employs the dynamic electrode displacement signal.

As shown in FIG. 3, the present embodiment relates to an on-line expulsion detection system based on intrinsic process signals for resistance spot welding process, including: a calculation and analysis module 10, a current signal acquisition module 9 and an intrinsic process signal acquisition module 8 respectively connected thereto, wherein the current signal acquisition module 9 is connected with a current sensor 5 installed on the electrode to collect a current signal, and the intrinsic process signal acquisition module 8 is connected with a pair of intrinsic process signal sensors 6 and 7 mounted on the two electrodes 2 and 3 to acquire intrinsic process signal, and the calculation and analysis module 10 calculates a predicted value of the expulsion metal according to the intrinsic process signal and the current signal.

The electrode cap 1, the upper electrode 2 and the upper electrode intrinsic process signal sensor 6 are placed in order on the upper surface of the workpiece 4 to be tested, the electrode cap 1, the lower electrode 3 and the lower electrode intrinsic process signal sensor 7 are placed in order on the lower surface of the workpiece 4 to be tested, and the current sensor 5 is put on the lower electrode 3.

The upper electrode intrinsic process signal sensor 6 is a linear displacement sensor; the lower electrode intrinsic process signal sensor 7 is a laser displacement sensor.

The workpiece 4 to be tested can be a plate, a pipe, a rod, a nail, a block and a combination thereof. The material can be steel, aluminum alloy, copper alloy, magnesium alloy, titanium alloy and a combination thereof.

The current sensor 5 is a Rogowski coil.

The computing and analysis module 10 includes a microprocessor, an industrial personal computer, a PLC, a monitor, a welding controller, a desktop, a laptop, a server, or a workstation. This embodiment employs a welding controller.

As shown in FIG. 4, the relationship graph is divided into three stages by welding current, specifically, the pre-weld squeezing stage $T_1$, the ohmic heating and welding stage $T_2$, and the post-weld hold stage $T_3$. The pre-weld squeezing stage $T_1$ refers to the time period from when the electrodes are closed to press the to-be-tested workpiece 4 to when the welding current is turned on. The ohmic heating and welding stage $T_2$ refers to the time period from when the welding current is turned on to when it is turned off. The post-weld p hold stage T refers to the time period from when the welding current is turned off to when the electrodes are opened.

As shown in FIG. 5, the expulsion judgment specifically comprises:

(1) During the ohmic heating and welding stage, the expulsion is determined to begin when the derivative of intrinsic process signal with respect to time is equal to the preset threshold A, that is, when it intersects the threshold horizontal line at point $Q_{ia}$, and the moment corresponding to the point $Q_{ia}$ is recorded as the start time $T_{ia}$; after the expulsion starts, the expulsion is determined to end when the derivative of intrinsic process signal with respect to time is again equal to the threshold A, that is, when it intersects the threshold horizontal line at point $Q_{ib}$, and the moment corresponding to the $Q_{ib}$ is recorded as the end time $T_{ib}$, and the occurrence of one weld expulsion is recorded as $F_i$, wherein: i represents the ith expulsion that occurs during the RSW process, and $0 \le i \le N$, where N is the total number of expulsion occurring during the RSW process.

(2) In the ohmic heating and welding stage, the intrinsic process signal points $P_{ia}$ and $P_{ib}$ corresponding to the start time $T_{ia}$ and the end time $T_{ib}$ of the i-th expulsion $F_i$ are extracted. The absolute difference of signal values $X_{ia}$ and $X_{ib}$ corresponding to the point $P_{ia}$ and $P_{ib}$, ie, $\Delta X_i = X_{ia} - X_{ib}$, is calculated as the intrinsic process signal feature $\Delta X_i$ corresponding to the i-th expulsion. The extraction of the accumulated feature refers to the combination of N intrinsic process signal feature $\Delta X_i$ to obtain the accumulated feature $\Delta X$ of the intrinsic process signal when N expulsions occur during the RSW process.

The combination may include calculating an arithmetic mean, a quadratic mean, a geometric mean, or a weighted average of N $\Delta X_i$. This embodiment preferably uses a geometric mean.

As shown in FIG. 6, the present embodiment sets the threshold A as 8 μm. The expulsion start time and end time are determined according to the intersection of the dynamic electrode displacement differential signal and the threshold horizontal line. It is found that the expulsion occurs only once, and is marked as $F_1$.

The expulsion metal volume refers to the ejected metal volume ΔV or expulsion metal weight ΔM calculated by accumulated feature ΔX and the electrode profile feature, wherein the expulsion metal weight ΔM is directly proportional to the ejected metal volume ΔV, and the proportion coefficient is the liquid metal density p of the to-be-tested workpiece 4, ie, ΔM=ρΔV, and $$\Delta V = \begin{cases} \frac{2}{3}\pi K_1\left[2R_t^3 - R_t^2\left(R_t - \frac{\Delta X}{2}\right) + \left(R_t - \frac{\Delta X}{2}\right)^3\right], & \Delta X < 2h_0 \\ \frac{2}{3}\pi K_1\left[2R_t^3 - R_t^2(R_t - h_0) + (R_t - h_0)^3 + \left(h_1 + h_0 - \frac{\Delta X}{2}\right)^3 - h_1^3 + \frac{3}{4}D^2\left(h_0 - \frac{\Delta X}{2}\right)\right], & \Delta X \geq 2h_0 \end{cases},$$

where: $K_1$ is the correction coefficient selected according to different intrinsic process signals; $R_t$ is the tip surface curvature radius of the electrode; $D_t$ is the tip face diameter of the electrode; D is the bottom diameter of the electrode; ΔX is the accumulated feature; $h_0$ and $h_1$ are feature heights and $$h_0 = R_t - \sqrt{R_t^2 - \frac{D_t^2}{4}},\ h_1 = \frac{\sqrt{D^2 - D_t^2}}{2}.$$

When the correction coefficient $K_1$ is set to 0.8 $\mu m^{-1}$, the expulsion metal volume in the RSW process can be calculated by the accumulated feature as follows.

$$\Delta V = \begin{cases} \frac{2}{5}\pi\left[2R_t^3 - R_t^2\left(R_t - \frac{\Delta X}{2}\right) + \left(R_t - \frac{\Delta X}{2}\right)^3\right], & \Delta X < 2h_0 \\ \frac{2}{5}\pi\left[2R_t^3 - R_t^2(R_t - h_0) + (R_t - h_0)^3 + \left(h_1 + h_0 - \frac{\Delta X}{2}\right)^3 - h_1^3 + \frac{3}{4}D^2\left(h_0 - \frac{\Delta X}{2}\right)\right], & \Delta X \geq 2h_0 \end{cases}$$

Then the expulsion metal weight ΔM can be calculated according to ΔM=ρΔV.

In this embodiment, the tip surface curvature radius $R_t$ of the electrode cap 1 is 50 mm, the tip face diameter $D_t$ of the electrode is 5 mm, the bottom diameter D of the electrode is 16 mm, and the liquid metal density ρ is 6.9 $kg/mm^3$. FIG. 7 shows the scatter diagram of the actual and predicted values of the expulsion metal weight in this embodiment. It can be seen that the predicted value and the actual value of the expulsion metal weight have a good linear correlation relationship. The determination coefficient is 0.9425, the root mean square error is 8 mg, and the prediction precision is high. The average calculation time of the predicted expulsion metal amount is 0.05 s, and the calculation speed is high.

Example 2

As shown in FIG. 2*b*, compared with Example 1, the electrode cap 1 of the present embodiment is a cone electrode with a spherical tip face, preferably a dynamic electrode force signal is used as an intrinsic process signal. The upper electrode intrinsic process signal sensor 6 is a weighing sensor, the lower electrode intrinsic process signal sensor 7 is a surface strain sensor, the current sensor 5 is a Hall current sensor, and the calculation and analysis module 10 employs a monitor.

As shown in FIG. 8, the present embodiment sets the threshold A to 30 N. The expulsion start time and end time are determined according to the intersection of the dynamic electrode force differential signal and the threshold horizontal line. It is found that the expulsion occurs only once, and is marked as $F_1$. The expulsion metal volume can be calculated by the accumulated feature amount in the RSW process as $$\Delta V = \begin{cases} \frac{2}{5}\pi\left[2R_t^3 - R_t^2\left(R_t - \frac{\Delta X}{2}\right) + \left(R_t - \frac{\Delta X}{2}\right)^3\right], & \Delta X < 2h_0 \\ \frac{2}{5}\pi\left[2R_t^3 - R_t^2(R_t - h_0) + (R_t - h_0)^3 + \left(h_1 + h_0 - \frac{\Delta X}{2}\right)^3 - h_1^3 + \frac{3}{4}D^2\left(h_0 - \frac{\Delta X}{2}\right)\right], & \Delta X \geq 2h_0 \end{cases}$$

where $K_2$ is the correction coefficient selected according to different intrinsic process signals, $R_t$ is the tip surface curvature radius of the electrode, $D_t$ is the tip face diameter of the electrode, D is the bottom diameter of the electrode, ΔX is the accumulated feature, $h_0$ is the feature height, and the calculation formula is $$h_0 = R_t - \sqrt{R_t^2 - \frac{D_t^2}{4}}.$$

Then the expulsion metal weight ΔM can be calculated according to ΔM=ρΔV.

In the present embodiment, the correction factor $K_2$ is set to 4 $N^{-1}$, the tip surface curvature radius $R_t$ of electrode cap 1 is 50 mm, the tip face diameter $D_t$ of the electrode is 5 mm, the top cone angle θ is 75 degrees, the bottom diameter D of the electrode is 16 mm, and the liquid metal density ρ is 6.9 $kg/mm^3$. FIG. 9 shows the scatter diagram of the actual and predicted values of the expulsion metal weight in this embodiment. It can be seen that the predicted value and the actual value of the expulsion metal weight have a good linear correlation relationship, where the determination coefficient is 0.9794, the root mean square error is 7.6 mg, and the prediction precision is high. The average calculation time of the predicted spatter metal amount is 0.06 s, and the calculation speed is high.

Example 3

As shown in FIG. 2*c*, compared with Example 1, the electrode cap 1 of the present embodiment is a ball head electrode. The bottom diameter D of the electrode cap 1 needs to be measured, and the calculation formula of the expulsion metal volume is:

$$\Delta V = \frac{K_3}{4}\left[\pi D^2 \Delta X - \frac{1}{3}\pi D^3 + \frac{1}{3}\pi (D - \Delta X)^3\right],$$

where: $K_3$ is the correction coefficient selected according to different intrinsic process signals.

Example 4

As shown in FIG. 2*d*, compared with Example 1, the electrode cap 1 of the present embodiment is a cylindrical electrode. The bottom diameter D of the electrode cap 1 needs to be measured, and the calculation formula of the expulsion metal volume is:

$$\Delta V = \frac{K_4}{4}\pi D^2 \Delta X,$$

wherein: $K_4$ is the correction coefficient selected according to different intrinsic process signals.

Example 5

As shown in FIG. 2*e*, compared to Example 1, the electrode cap 1 of the present embodiment is a truncated cone electrode, and it is necessary to measure the bottom diameter D of the electrode cap 1, the tip face diameter $D_t$ and the top cone angle θ, and the calculation formula of the expulsion metal volume is:

$$\Delta V = \frac{\pi}{12} K_5 \tan\theta\left[(D_t + \Delta X \cot\theta)^3 - D_t^3\right],$$

wherein: $K_5$ is the correction coefficient selected according to different intrinsic process signals.

Example 6

As shown in FIG. 2*f*, compared with Example 1, the electrode cap 1 of the present embodiment is a cylindrical electrode with a spherical tip face, the bottom diameter D and the tip surface curvature radius $R_t$ are measured, and the calculation formula of the expulsion metal volume is as follows:

$$\Delta V = \begin{cases} \frac{2}{3}\pi K_6\left[2R_t^3 - 3R_t^2\left(R_t - \frac{\Delta X}{2}\right) + \left(R_t - \frac{\Delta X}{2}\right)^3\right], & \Delta X < 2h_2 \\ \frac{\pi}{6} K_6\left[8R_t^3 - 12R_t^2(R_t - h_2) + 4(R_t - h_2)^3 + 3D^2\left(\frac{\Delta X}{2} - h_2\right)\right], & \Delta X \geq 2h_2 \end{cases},$$

where $K_6$ is the correction coefficient selected according to different intrinsic process signals, $h_2$ is the feature height and $$h_2 = R_t - \sqrt{R_t^2 - \frac{D^2}{4}}.$$

Compared with the prior art, the present method can predict the expulsion metal amount in real time based on the calculation formula of the electrode profile feature and the intrinsic process signal feature. It can realize the on-line quantitative evaluation of the expulsion severity during the RSW process, and can overcome the defect of the traditional technology which relies on manual detection. Compared with the previous visual or manual detection method, the present method achieves automatic detection of the expulsion intensity, significantly improves the detection efficiency and accuracy. The high calculation speed and low requirement on the hardware system makes it suitable for various RSW application scenes. Meanwhile, the influence of different electrodes shapes is considered, so the applicability is high. A good linear relationship is found between the predicted and actually measured expulsion metal amount, and the detection precision is high.

The above mentioned specific embodiments may be partially adjusted in different ways by technicians in this field without deviating from the principle and purpose of the invention. The scope of protection of the invention shall be subject to the claim and shall not be limited by the above mentioned embodiments, and each implementation scheme within the scope shall be subject to the restriction of the invention.

What is claimed is:

1. An on-line expulsion detection method for resistance spot welding process based on an intrinsic process signal, characterized in that, the intrinsic process signal and a current signal output from sensors installed at two electrode caps are by collected in real time during a welding process and a relationship graph is developed; expulsion judgment is carried out based on a relationship graph to obtain an expulsion frequency, a single intrinsic process signal feature and an accumulated feature; an expulsion metal volume is calculated according to the accumulated feature and profile features of one electrode cap of the electrode caps to obtain a predicted expulsion metal amount; the intrinsic process signal comprises: a dynamic resistance signal, a dynamic electrode force signal, a dynamic electrode displacement signal, an acoustic emission signal and an ultrasonic signal; the profile features of the electrode cap comprise: a bottom diameter, a tip face diameter, a tip surface curvature, and a cone angle; wherein the expulsion metal volume is calculated by the following steps:

a domed electrode with a spherical tip face:

$$\Delta V = \begin{cases} \frac{2}{3}\pi K_1\left[2R_t^3 - R_t^2\left(R_t - \frac{\Delta X}{2}\right) + \left(R_t - \frac{\Delta X}{2}\right)^3\right], & \Delta X < 2h_0 \\ \frac{2}{3}\pi K_1\left[2R_t^3 - R_t^2(R_t - h_0) + (R_t - h_0)^3 + \left(h_1 + h_0 - \frac{\Delta X}{2}\right)^3 - \right. \\ \left. h_1^3 + \frac{3}{4}D^2\left(h_0 - \frac{\Delta X}{2}\right)\right], & \Delta X \geq 2h_0 \end{cases}$$

wherein: $K_1$ is the correction coefficient selected according to different intrinsic process signals, $R_t$ is the tip surface curvature radius of the electrode, $D_t$ is the tip face diameter of the electrode, D is the bottom diameter of the electrode, ΔX is the accumulated feature, $h_0$ and $h_1$ are feature heights and $$h_0 = R_t - \sqrt{R_t^2 - \frac{D_t^2}{4}} \text{ and } h_1 = \frac{\sqrt{D^2 - D_t^2}}{2};$$

a cone electrode with a spherical tip face:

$$\Delta V = \begin{cases} \frac{2}{3}\pi K_2\left[2R_t^3 - R_t^2\left(R_t - \frac{\Delta X}{2}\right) + \left(R_t - \frac{\Delta X}{2}\right)^3\right], & \Delta X < 2h_0 \\ \frac{2}{3}\pi K_2\left[2R_t^3 - 3R_t^2(R_t - h_0) + (R_t - h_0)^3 + \left(\frac{D_t}{2} + \right.\right. \\ \left.\left.\left(\frac{\Delta X}{2} - h_0\right)\cot\theta\right)^3 \tan\theta - \left(\frac{D_t}{2}\right)^3 \tan\theta\right], & \Delta X \geq 2h_0 \end{cases}$$

wherein $K_2$ is the correction coefficient selected according to different intrinsic process signals, $R_t$ is the tip surface curvature radius of the electrode, $D_t$ is tip face diameter of the electrode, ΔX is the accumulated feature, $h_0$ is the feature height, and the calculation formula is $$h_0 = R_t - \sqrt{R_t^2 - \frac{D_t^2}{4}};$$

a ball-head electrode:

$$\Delta V = \frac{K_3}{4}\left[\pi D^2 \Delta X - \frac{1}{3}\pi D^3 + \frac{1}{3}\pi(D - \Delta X)^3\right]$$

wherein $K_3$ is the correction coefficient selected according to different intrinsic process signals, D is the bottom diameter of the electrode, ΔX is the accumulated feature; a flat-top electrode:

$$\Delta V = \frac{K_4}{4}\pi D^2 \Delta X$$

where $K_4$ is the correction coefficient selected according to different intrinsic process signals, D is the bottom diameter of the electrode, ΔX is the accumulated feature quantity;

a flat cone top electrode:

$$\Delta V = \frac{\pi}{12}K_5 \tan\theta\left[(D_t + \Delta X \cot\theta)^3 - D_t^3\right]$$

wherein: $K_5$ is a correction coefficient selected according to different intrinsic process signals, $D_t$ is the tip face diameter, θ is the cone angle, and ΔX is the accumulated feature;

a cylindrical electrode with a spherical tip face:

$$\Delta V = \begin{cases} \frac{2}{3}\pi K_6\left[2R_t^3 - 3R_t^2\left(R_t - \frac{\Delta X}{2}\right) + \left(R_t - \frac{\Delta X}{2}\right)^3\right], & \Delta X < 2h_2 \\ \frac{\pi}{6}K_6\left[8R_t^3 - 12R_t^2(R_t - h_2) + 4(R_t - h_2)^3 + 3D^2\left(\frac{\Delta X}{2} - h_2\right)\right], & \Delta X \geq 2h_2 \end{cases}$$

wherein: $K_6$ is the correction coefficient selected according to different intrinsic process signals, D is the bottom diameter of the electrode cap, $R_t$ is the tip surface curvature radius of the electrode, ΔX is the accumulated feature, and $h_2$ is the feature height and $$h_2 = R_t - \sqrt{R_t^2 - \frac{D^2}{4}}.$$

2. The method according to claim 1, wherein the expulsion judgment refers to that the expulsion is determined to begin when a derivative of the intrinsic process signal with respect to time is equal to a preset threshold during an ohmic heating and welding stage; after the expulsion starts, the expulsion is determined to end when the derivative of the intrinsic process signal with respect to time is again equal to a preset threshold, and an absolute amplitude difference between the intrinsic process signal corresponding to the expulsion beginning and ending moment is taken as the single intrinsic process feature; several single intrinsic process features of the intrinsic process signal are combined to obtain the accumulated feature when multiple expulsions occur in the welding process.

3. The method according to claim 1, wherein the electrode caps comprise: a cylinder electrode, a dome electrode, a curved-top cone electrode, a ball head electrode, a flat-top electrode, a flat cone electrode and a truncated cone electrode.

4. The method according to claim 1, characterized in that, the relationship graph is divided into three stages by a welding current signal, specifically, a pre-weld squeezing stage $T_1$, the ohmic heating and welding stage $T_2$, and the post-weld hold stage $T_3$, wherein the pre-weld squeezing stage $T_1$ refers to the time period from when the electrodes are closed to press the to-be-tested workpiece 4 to when the welding current is turned on; the ohmic heating and welding stage $T_2$ refers to the time period from when the welding current is turned on to when it is turned off; the post-weld p hold stage $T_3$ refers to the time period from when the welding current is turned off to when the electrodes are opened.

5. The method according to claim 4, wherein the expulsion judgment specifically comprises:

during the ohmic heating and welding stage, the expulsion is determined to begin when the derivative of intrinsic process signal with respect to time is equal to a preset threshold A, when the derivative of intrinsic process signal intersects a threshold horizontal line at point $Q_{ia}$, and a moment corresponding to the point $Q_{ia}$ is recorded as a start time $T_{ia}$; after the expulsion starts, the expulsion is determined to end when the derivative of intrinsic process signal with respect to time is again equal to the threshold A, when the derivative of intrinsic process signal intersects the threshold horizontal line at point $Q_{ib}$, and a moment corresponding to the $Q_{ib}$ is recorded as an end time $T_{ib}$, and an occurrence of one weld expulsion is recorded as $F_i$, wherein: i represents the ith expulsion that occurs during a RSW process, and $0 \leq i \leq N$, where N is the total number of expulsion occurring during the RSW process;

in the ohmic heating and welding stage, the intrinsic process signal points $P_{ia}$ and $P_{ib}$ corresponding to the start time $T_{ia}$ and the end time $T_{ib}$ of the i-th expulsion $F_i$ are extracted; the absolute difference of signal values $X_{ia}$ and $X_{ib}$ corresponding to the point $P_{ia}$ and $P_{ib}$, ie, $\Delta X_i = X_{ia} - X_{ib}$, is calculated as the intrinsic process signal feature $\Delta X_i$ corresponding to the i-th expulsion; the extraction of the accumulated feature refers to the combination of N intrinsic process signal feature $\Delta X_i$ to obtain the accumulated feature $\Delta X$ of the intrinsic process signal when N expulsions occur during the RSW process.

6. A system for implementing the method of claim 1, characterized in that, calculation and analysis modules and a current signal acquisition module attached to them respectively, and an intrinsic process signal acquisition module, wherein the current signal acquisition module collecting the current signal is connected with current sensors installed at the electrodes; the intrinsic process signal acquisition module collecting the intrinsic process signals is respectively connected with intrinsic process signal sensors installed at the two electrode caps; the calculation and analysis modules calculate the predicted amount of the expulsion metal according to the intrinsic process signal and the current signal.

* * * * *